US009295527B2

(12) United States Patent
Kirschenman et al.

(10) Patent No.: US 9,295,527 B2
(45) Date of Patent: *Mar. 29, 2016

(54) ROBOTIC CATHETER SYSTEM WITH DYNAMIC RESPONSE

(71) Applicant: St. Jude Medical, Atrial Fibrillation Division, Inc., St. Paul, MN (US)

(72) Inventors: Mark B. Kirschenman, Waverly, MN (US); John A. Hauck, Shoreview, MN (US); Andrew P. Skypeck, Andover, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 40 days.

This patent is subject to a terminal disclaimer.

(21) Appl. No.: 14/151,266

(22) Filed: Jan. 9, 2014

(65) Prior Publication Data

US 2014/0194898 A1 Jul. 10, 2014

Related U.S. Application Data

(63) Continuation of application No. 12/933,065, filed as application No. PCT/US2009/038597 on Mar. 27, 2009, now Pat. No. 8,641,664.

(60) Provisional application No. 61/040,143, filed on Mar. 27, 2008, provisional application No. 61/099,904, filed on Sep. 24, 2008, provisional application No. 61/142,008, filed on Dec. 31, 2008.

(51) Int. Cl.
*A61M 31/00* (2006.01)
*A61M 37/00* (2006.01)
(Continued)

(52) U.S. Cl.
CPC ............. *A61B 19/2203* (2013.01); *A61B 19/20* (2013.01); *A61M 25/0067* (2013.01); *A61B 2019/2211* (2013.01); *A61B 2019/2242* (2013.01); *A61B 2019/464* (2013.01)

(58) Field of Classification Search
CPC ............... A61B 19/20; A61B 19/2203; A61B 2019/2211; A61B 2019/2242; A61B 2019/464; A61M 25/0067
See application file for complete search history.

(56) References Cited

U.S. PATENT DOCUMENTS

| 3,091,130 A | 5/1963 | Payerle et al. |
| 3,605,725 A | 9/1971 | Bentov |

(Continued)

FOREIGN PATENT DOCUMENTS

| EP | 0151479 | 8/1985 |
| EP | 09094796 | 3/1999 |

(Continued)

OTHER PUBLICATIONS

International Search Report & Written Opinion, PCT/US2009069712, Feb. 25, 2010.

(Continued)

*Primary Examiner* — Rebecca E Eisenberg
(74) *Attorney, Agent, or Firm* — Dykema Gossett PLLC

(57) ABSTRACT

An apparatus for maintaining a robotic catheter system in a responsive state includes a catheter, a plurality of linear translatable control elements, and a controller. In an embodiment, the catheter includes a proximal portion, a distal portion, and at least two steering wires. The steering wires may be configured at one end to control the movement of at least a portion of the distal portion of the catheter and at the other end for connection to a control member. In an embodiment, each control element may be configured to engage or interface with a respective control member, and the controller may be configured to measure a force exerted on at least one control member by a respective control element and further configured to linearly translate the control element to substantially maintain a force within a predetermined range.

20 Claims, 15 Drawing Sheets

(51) Int. Cl.
*A61B 19/00* (2006.01)
*A61M 25/00* (2006.01)

(56) References Cited

U.S. PATENT DOCUMENTS

| | | |
|---|---|---|
| 3,893,449 A | 7/1975 | Lee et al. |
| 4,160,508 A | 7/1979 | Frosch et al. |
| 4,348,556 A | 9/1982 | Gettig et al. |
| 4,393,728 A | 7/1983 | Larson et al. |
| 4,543,090 A | 9/1985 | McCoy |
| 4,758,222 A | 7/1988 | McCoy |
| 4,784,042 A | 11/1988 | Paynter |
| 4,802,487 A | 2/1989 | Martin et al. |
| 4,884,557 A | 12/1989 | Takehana et al. |
| 4,962,448 A | 10/1990 | DeMaio et al. |
| 4,974,151 A | 11/1990 | Advani et al. |
| 5,078,140 A | 1/1992 | Kwoh |
| 5,107,080 A | 4/1992 | Rosen et al. |
| 5,170,817 A | 12/1992 | Sunderland et al. |
| 5,238,005 A | 8/1993 | Imran |
| 5,298,930 A | 3/1994 | Asakura et al. |
| 5,303,148 A | 4/1994 | Mattson et al. |
| 5,318,525 A | 6/1994 | West et al. |
| 5,339,799 A | 8/1994 | Kami et al. |
| 5,396,266 A | 3/1995 | Brimhall et al. |
| 5,410,638 A | 4/1995 | Colgate et al. |
| 5,441,483 A | 8/1995 | Avitall |
| 5,449,345 A | 9/1995 | Taylor et al. |
| 5,520,644 A | 5/1996 | Imran |
| 5,533,967 A | 7/1996 | Imran |
| 5,545,200 A | 8/1996 | West et al. |
| 5,579,442 A | 11/1996 | Kimoto et al. |
| 5,607,158 A | 3/1997 | Chan |
| 5,607,462 A | 3/1997 | Imran |
| 5,623,582 A | 4/1997 | Rosenberg |
| 5,630,783 A | 5/1997 | Steinberg |
| 5,661,253 A | 8/1997 | Aoki |
| 5,706,827 A | 1/1998 | Ehr et al. |
| 5,784,542 A | 7/1998 | Ohm et al. |
| 5,791,908 A | 8/1998 | Gillio |
| 5,800,178 A | 9/1998 | Gillio |
| 5,807,377 A | 9/1998 | Madhani et al. |
| 5,808,665 A | 9/1998 | Green |
| 5,828,813 A | 10/1998 | Ohm |
| 5,854,622 A | 12/1998 | Brannon |
| 5,861,024 A | 1/1999 | Rashidi |
| 5,876,325 A | 3/1999 | Mizuno et al. |
| 5,897,488 A | 4/1999 | Ueda |
| 5,913,820 A | 6/1999 | Bladen et al. |
| 6,040,758 A | 3/2000 | Sedor et al. |
| 6,063,095 A | 5/2000 | Wang et al. |
| 6,113,395 A | 9/2000 | Hon |
| 6,201,196 B1 | 3/2001 | Wergen |
| 6,233,476 B1 | 5/2001 | Strommer et al. |
| 6,233,504 B1 | 5/2001 | Das et al. |
| 6,290,683 B1 | 9/2001 | Erez et al. |
| 6,348,911 B1 | 2/2002 | Rosenberg et al. |
| 6,358,207 B1 | 3/2002 | Lathbury et al. |
| 6,385,509 B2 | 5/2002 | Das et al. |
| 6,396,232 B2 | 5/2002 | Haanpaa et al. |
| 6,432,112 B2 | 8/2002 | Brock et al. |
| 6,498,944 B1 | 12/2002 | Ben-Haim et al. |
| 6,500,167 B1 | 12/2002 | Webster |
| 6,522,141 B2 | 2/2003 | Debbins et al. |
| 6,540,685 B1 | 4/2003 | Rhoads et al. |
| 6,671,533 B2 | 12/2003 | Chen et al. |
| 6,709,667 B1 | 3/2004 | Lowe et al. |
| 6,785,358 B2 | 8/2004 | Johnson et al. |
| 6,850,252 B1 | 2/2005 | Hoffberg |
| 6,869,390 B2 | 3/2005 | Elliot et al. |
| 6,869,396 B2 | 3/2005 | Belson |
| 6,968,223 B2 | 11/2005 | Hanover |
| 7,016,469 B2 | 3/2006 | Johnson et al. |
| 7,193,521 B2 | 3/2007 | Moberg et al. |
| 7,197,354 B2 | 3/2007 | Sobe |
| 7,199,790 B2 | 4/2007 | Rosenberg et al. |
| 7,247,139 B2 | 7/2007 | Yudkovitch et al. |
| 7,263,397 B2 | 8/2007 | Hauck et al. |
| 7,276,044 B2 | 10/2007 | Ferry et al. |
| 7,386,339 B2 | 6/2008 | Strommer et al. |
| 7,465,288 B2 | 12/2008 | Dudney et al. |
| 7,672,849 B2 | 3/2010 | Yudkovitch et al. |
| 7,698,966 B2 | 4/2010 | Gosselin |
| 7,742,803 B2 | 6/2010 | Viswanathan et al. |
| 7,850,642 B2 | 12/2010 | Moll et al. |
| 7,880,717 B2 | 2/2011 | Berkley et al. |
| 7,945,546 B2 | 5/2011 | Bliss et al. |
| 7,963,288 B2 | 6/2011 | Rosenberg et al. |
| 8,164,573 B2 | 4/2012 | DaCosta et al. |
| 8,317,744 B2 | 11/2012 | Kirschenman |
| 8,317,745 B2 | 11/2012 | Kirschenman et al. |
| 8,332,072 B1 | 12/2012 | Schaible et al. |
| 8,390,438 B2 | 3/2013 | Olson et al. |
| 8,416,203 B2 | 4/2013 | Tsui |
| 8,560,118 B2 | 10/2013 | Greer et al. |
| 8,926,511 B2 | 1/2015 | Bar-Tal |
| 2001/0018591 A1 | 8/2001 | Brock et al. |
| 2001/0025183 A1 | 9/2001 | Shahidi |
| 2002/0068868 A1 | 6/2002 | Thompson et al. |
| 2002/0072704 A1 | 6/2002 | Mansouri-Ruiz |
| 2002/0087048 A1 | 7/2002 | Brock et al. |
| 2002/0184055 A1 | 12/2002 | Naghavi et al. |
| 2003/0018232 A1 | 1/2003 | Elliott et al. |
| 2003/0050733 A1 | 3/2003 | Wang et al. |
| 2003/0114962 A1 | 6/2003 | Niemeyer |
| 2003/0121382 A1 | 7/2003 | Morson |
| 2004/0050247 A1 | 3/2004 | Topping |
| 2004/0068173 A1 | 4/2004 | Viswanathan |
| 2004/0133189 A1 | 7/2004 | Sakurai |
| 2004/0138530 A1 | 7/2004 | Kawai et al. |
| 2004/0146388 A1 | 7/2004 | Khajepour et al. |
| 2004/0193239 A1 | 9/2004 | Falwell |
| 2004/0223636 A1 | 11/2004 | Edic et al. |
| 2004/0243147 A1 | 12/2004 | Lipow |
| 2005/0038333 A1 | 2/2005 | Sra et al. |
| 2005/0075538 A1 | 4/2005 | Banik et al. |
| 2005/0172405 A1 | 8/2005 | Menkedick et al. |
| 2005/0203382 A1 | 9/2005 | Govari et al. |
| 2005/0222554 A1 | 10/2005 | Wallace et al. |
| 2005/0234293 A1 | 10/2005 | Yamamoto et al. |
| 2005/0234320 A1 | 10/2005 | Balasubramanian |
| 2006/0052664 A1 | 3/2006 | Julian et al. |
| 2006/0089637 A1 | 4/2006 | Werneth et al. |
| 2006/0137476 A1 | 6/2006 | Bull et al. |
| 2006/0155321 A1 | 7/2006 | Bressler et al. |
| 2006/0276775 A1 | 12/2006 | Rosenberg et al. |
| 2006/0293643 A1 | 12/2006 | Wallace et al. |
| 2007/0016008 A1 | 1/2007 | Schoenefeld |
| 2007/0022384 A1 | 1/2007 | Abbott et al. |
| 2007/0043338 A1 | 2/2007 | Moll et al. |
| 2007/0060833 A1 | 3/2007 | Hauck |
| 2007/0073137 A1 | 3/2007 | Schoenefeld et al. |
| 2007/0100254 A1 | 5/2007 | Murakami et al. |
| 2007/0120512 A1 | 5/2007 | Albu-Schaffer et al. |
| 2007/0135803 A1 | 6/2007 | Belson |
| 2007/0142726 A1 | 6/2007 | Carney et al. |
| 2007/0172803 A1 | 7/2007 | Hannaford et al. |
| 2007/0185404 A1 | 8/2007 | Hauck et al. |
| 2007/0185485 A1 | 8/2007 | Hauck |
| 2007/0185486 A1 | 8/2007 | Hauck et al. |
| 2007/0197896 A1 | 8/2007 | Moll et al. |
| 2007/0197939 A1 | 8/2007 | Wallace et al. |
| 2007/0198008 A1 | 8/2007 | Hauck et al. |
| 2007/0233044 A1 | 10/2007 | Wallace et al. |
| 2007/0233045 A1 | 10/2007 | Weitzner et al. |
| 2007/0270685 A1 | 11/2007 | Kang et al. |
| 2007/0276214 A1 | 11/2007 | Dachille et al. |
| 2007/0298877 A1 | 12/2007 | Rosenberg et al. |
| 2008/0009791 A1 | 1/2008 | Cohen et al. |
| 2008/0013809 A1 | 1/2008 | Zhu et al. |
| 2008/0112842 A1 | 5/2008 | Edwards |
| 2008/0201847 A1 | 8/2008 | Menkedick et al. |
| 2008/0312536 A1 | 12/2008 | Dala-Krishna |
| 2009/0012533 A1 | 1/2009 | Barbagli et al. |

(56) References Cited

U.S. PATENT DOCUMENTS

| | | |
|---|---|---|
| 2009/0033623 A1 | 2/2009 | Lin |
| 2009/0061928 A1 | 3/2009 | Lee et al. |
| 2009/0123111 A1 | 5/2009 | Udd |
| 2009/0137952 A1 | 5/2009 | Ramamurthy et al. |
| 2009/0177454 A1 | 7/2009 | Bronstein et al. |
| 2009/0192519 A1 | 7/2009 | Omori |
| 2009/0195514 A1 | 8/2009 | Glynn et al. |
| 2009/0247993 A1 | 10/2009 | Kirschenman et al. |
| 2009/0264156 A1 | 10/2009 | Burghardt et al. |
| 2009/0322697 A1 | 12/2009 | Cao |
| 2010/0066676 A1 | 3/2010 | Kramer et al. |
| 2010/0073150 A1 | 3/2010 | Olson et al. |
| 2010/0079386 A1 | 4/2010 | Scott et al. |
| 2010/0082039 A1 | 4/2010 | Mohr et al. |
| 2010/0103127 A1 | 4/2010 | Park et al. |
| 2010/0256558 A1 | 10/2010 | Olson et al. |
| 2010/0268067 A1 | 10/2010 | Razzaque et al. |
| 2010/0314031 A1 | 12/2010 | Heideman et al. |
| 2011/0040547 A1 | 2/2011 | Gerber et al. |
| 2011/0128555 A1 | 6/2011 | Rotschild et al. |
| 2011/0137156 A1 | 6/2011 | Razzaque et al. |
| 2011/0152882 A1 | 6/2011 | Wenderow et al. |
| 2011/0289441 A1 | 11/2011 | Venon et al. |
| 2011/0306986 A1 | 12/2011 | Lee |
| 2012/0071891 A1 | 3/2012 | Itkowitz et al. |
| 2012/0133601 A1 | 5/2012 | Marshall et al. |
| 2012/0277663 A1 | 11/2012 | Millman et al. |
| 2013/0006268 A1 | 1/2013 | Swarup et al. |
| 2013/0154913 A1 | 6/2013 | Genc et al. |
| 2013/0165854 A1 | 6/2013 | Sandhu et al. |
| 2013/0176220 A1 | 7/2013 | Merschon et al. |
| 2013/0179162 A1 | 7/2013 | Merschon et al. |

FOREIGN PATENT DOCUMENTS

| | | |
|---|---|---|
| GB | 2211280 | 6/1989 |
| GB | 2397177 | 7/2004 |
| JP | S60221280 | 11/1985 |
| JP | H06344285 | 12/1994 |
| JP | H8-280709 | 10/1996 |
| JP | H10216238 | 8/1998 |
| JP | 2003024336 | 1/2003 |
| JP | 2007325936 | 12/2007 |
| WO | 9320535 | 10/1993 |
| WO | 9639944 | 12/1996 |
| WO | 03049596 | 6/2003 |
| WO | 2006120666 | 11/2006 |
| WO | 2007088208 | 8/2007 |
| WO | 2007098494 | 8/2007 |
| WO | 2007120329 | 10/2007 |
| WO | 2007/136803 | 11/2007 |
| WO | 2007136803 | 11/2007 |
| WO | 2007143859 | 12/2007 |
| WO | 2007146325 | 12/2007 |
| WO | 2008045831 | 4/2008 |
| WO | 2008/103212 | 8/2008 |
| WO | 2008101228 | 8/2008 |
| WO | 2009120940 | 10/2009 |
| WO | 2009120982 | 10/2009 |
| WO | 2009120992 | 10/2009 |
| WO | 2010025338 | 3/2010 |
| WO | 2010059179 | 5/2010 |
| WO | 2010068783 | 6/2010 |
| WO | 2010107916 | 9/2010 |

OTHER PUBLICATIONS

Supplementary European Search Report for EP Application No. 11763410.5, dated Jun. 10, 2015. 7 pages.

Title: The Aurora Electromagnetic Tracking System, Aurora Electromagnetic Measurement System—3D Tracking for Medical Guidance Citation: Northern Digital, Inc. <URL: http://www.ndigital.com/medical/aurora.pho?act=print> Publication Date: (actual publication date unknown).

Title: International Search Report Citation: PCT Application No. PCT/US2009/038525 Publication Date: May 27, 2009 2 pages.

Title: International Search Report Citation: PCT Application No. PCT/US2009/038531 Publication Date: May 19, 2009 3 pages.

Title: International Search Report Citation: PCT Application No. PCT/US2009/038533 Publication Date: Jun. 17, 2009 2 pages.

Title: International Search Report Citation: PCT Application No. PCT/US2009/038618 Publication Date: May 22, 2009 2 pages.

Title: International Search Report Citation: PCT Application No. PCT/US2009/038597 Publication Date: May 18, 2009 2 pages.

Title: International Search Report Citation: PCT Application No. PCT/US2009/038534 Publication Date: May 27, 2009 2 pages.

Title: International Search Report Citation: PCT Application No. PCT/US2009/038536 Publication Date: May 28, 2009 2 pages.

Title: International Search Report Citation: PCT Application No. PCT/US2009/058121 Publication Date: Nov. 19, 2009 2 pages.

Title: Supplemental European Search Report Citation: EP Application No. 09724550.0 Publication Date: Jul. 10, 2012 6 pages.

Title: Supplemental European Search Report Citation: EP Application No. 09723739.0 Publication Date: Jul. 10, 2012 6 pages.

Title: Supplemental European Search Report Citation: EP Application No. 09726364.4 Publication Date: Jan. 22, 2013 7 pages.

Title: International Search Report Citation: PCT Application No. PCT/US2011/030656 Publication Date: Jun. 13, 2011 8 pages.

Title: Supplemental European Search Report Citation: EP Application No. 11763450.1 Publication Date: Oct. 29, 2014 9 pages.

Title: Apple Wins Strategic Multitouch and Music Tempo Workout Patents Citation: Patently Apple <URL: http://www.patentlyapple.com/patently-apple/2010/04/apple-wins-strategic-multitouch-music-tempo-workout-patents.html> Publication Date: (actual publication date unknown).

Polaris Family of Optical Tracking Systems, Polaris Vicra & Spectra—Optical Measurement Systems for Medical Citation: Northern Digital Inc. <URL: http://www.ndigital.com/medical/polarisfamily.php?act=print> Publication Date: (actual publication date unknown).

Author: LaBelle, Kathryn Title: Evaluation of Kinect Joint Tracking for Clinical and In-Home Stroke Rehabilitation Tools Citation: <http://netscale.cse.nd.edu/twiki/pub/Edu/KinectRehabilitation/Eval_of_Kinect_for_Rehab.pdf> Publication Date: Dec. 2011.

Author: Padoy, Nicolas Title: Needle Insertion Revisted (tele-surgery in depth), (online) Citation: The John Hopkins University <URL: http://www.youtube.com/watch?v=YsY_A0kLh-g> Publication Date: Jan. 2011.

Title: Emotiv EPOC Software Development Kit—EPOC neuroheadset (online) Citation: <URL: http://www.emotiv.com/store/hardware/epoc/bci/epoc-neuroheadseU> Publication Date: (actual publication date unknown).

Title: Emotiv—Brain Computer Interface Technology (online) Citation: <URL: http://www.emotiv.com> Publication Date: (actual publication date unknown).

Title: Wii Remote—Wikipedia, the free encyclopedia (online) Citation: <URL: http://en.wikipedia.org/wiki/Wii_Remote> Publication Date: (actual publication date unknown).

Title: About the Kinect for Windows SDK—Microsoft Research (online) Citation: <URL: http://research.microsoft.com/en-us/um/redmond/projects/kinectsdk/about.aspx> Publication Date: (actual publication date unknown).

Title: Kinect—Wikipedia, the free encyclopedia (online) Citation: <URL: http://en.wikipedia.org/wiki/Kinect> Publication Date: (actual publication date unknown).

Title: International Search Report & Written Opinion Citation: PCT/US2012/031008 Publication Date: Jul. 20, 2012.

Title: International Search Report and Citation : PCT/US2011/030764 Publication Date: Jun. 15, 2011.

Title: Supplemental European Search Report Citation: EP Application No. 09725131.8 Publication Date: Feb. 20, 2013 7 pages.

Robot.pdf (Robot-Definition Robot at Dictionary.com, Oct. 27, 2015, http://dictionary.reference.com/browse/robot, pp. 1-5).

ROBOTIC CATHETER SYSTEM WITH DYNAMIC RESPONSE

CROSS REFERENCE TO RELATED APPLICATIONS

This application is a continuation of U.S. application Ser. No. 12/933,065, filed 16 Sep. 2010, which is a national stage filing and claims priority to international application no. PCT/US2009/038597, filed 27 Mar. 2009, which claims the benefit of U.S. provisional application Nos. 61/040,143, filed 27 Mar. 2008; 61/099,904, filed 24 Sep. 2008; and 61/142,008, filed 31 Dec. 2008, the entire disclosures of which are hereby incorporated by reference as though fully set forth herein.

BACKGROUND OF THE INVENTION a. Field of the Invention

This invention relates to a robotic catheter system and method for automated control of a catheter and related components, including a control system capable of being used in conjunction with a robotic catheter system to provide a certain or desired minimal tension on catheter steering wires in connection with medical applications or procedures.

b. Background Art

Electrophysiology catheters are used in a variety of diagnostic and/or therapeutic medical procedures to correct conditions such as atrial arrhythmia, including for example, ectopic atrial tachycardia, atrial fibrillation, and atrial flutter. Arrhythmia can cause a variety of serious medical conditions including irregular heart rates, loss of synchronous atrioventricular contractions, and stasis of blood flow.

Typically in a procedure, a catheter is manipulated through a patient's vasculature to, for example, a patient's heart, and carries one or more electrodes which may be used for mapping, ablation, diagnosis, and/or other treatments. After being positioned at an intended site, the catheter may be used to provide therapeutic treatment to the patient, such treatment may include radio frequency (RF) ablation, cryoablation, laser, chemicals, high-intensity focused ultrasound, or various other treatments. An ablation catheter commonly imparts ablative energy or chemicals to cardiac tissue to create a lesion in the cardiac tissue. The lesion can disrupt undesirable electrical pathways and serve to limit or prevent stray electrical signals that can lead to arrhythmias. Such treatments can require precise control of the catheter during manipulation to and at the treatment site, which can oftentimes be a function of a user's skill level.

The inventors herein have recognized a desire for a system and method for more precise and dynamic automated or semi-automated control of a catheter and its related components, for example, for diagnostic, therapeutic, mapping and ablative procedures, that help to minimize and/or eliminate procedural variability attendant to a user's skill level. The inventors herein have also recognized a need for a system and method for performing user-specified procedures at the patient site or from a remote location.

BRIEF SUMMARY OF THE INVENTION

An apparatus for maintaining a robotic catheter system in a responsive state includes a catheter, a plurality of linear translatable control elements, and a controller. In an embodiment, the catheter includes a proximal portion, a distal portion, and at least two steering wires. The steering wires may be configured at one end to control the movement of at least a portion of the distal portion of the catheter and at the other end for connection to a control member. In an embodiment, each control element may be configured to engage or interface with a respective control member, and the controller may be configured to measure a force exerted on at least one control member by a respective control element and further configured to linearly translate the control element to substantially maintain a force within a predetermined range.

BRIEF DESCRIPTION OF THE DRAWINGS

The drawings illustrate the design and utility of the illustrated embodiments of the invention, in which similar elements are referred to by common reference numerals, and in which.

DETAILED DESCRIPTION OF EMBODIMENTS OF THE INVENTION

Figure 1:
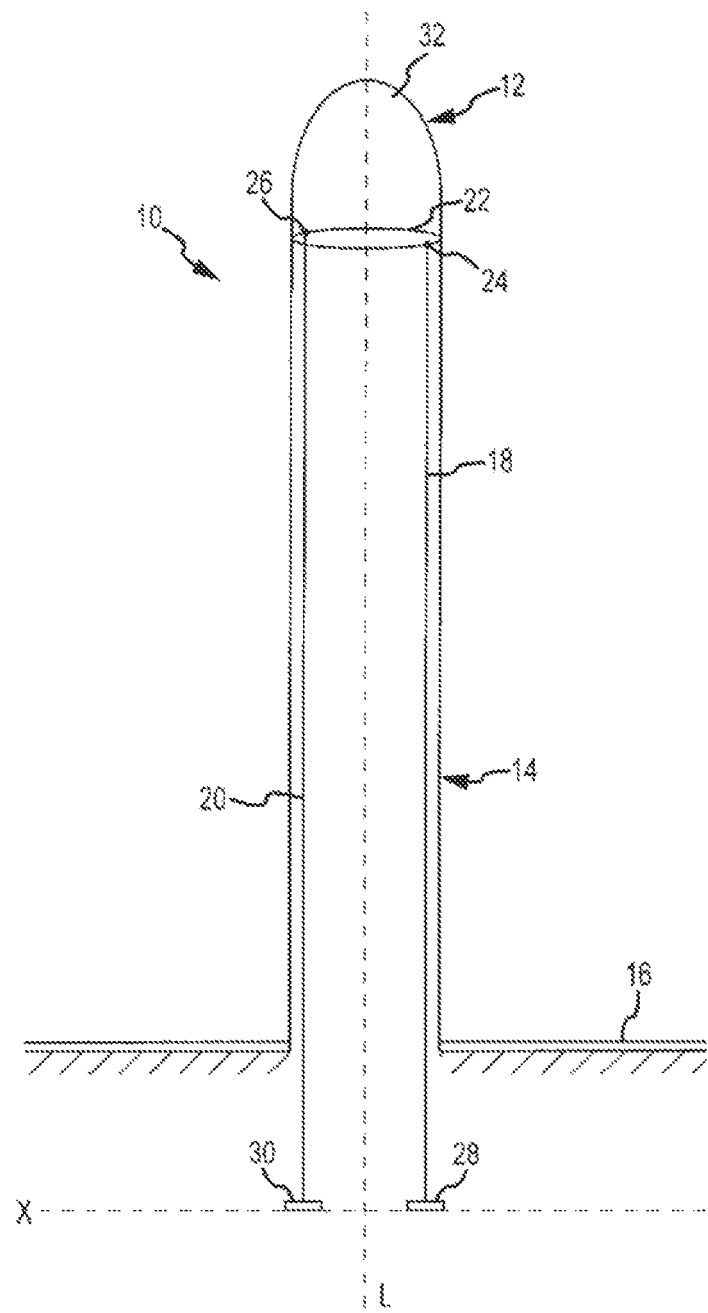
FIG. 1 is a general representation of a catheter according to an embodiment of the invention, shown in an undeflected state.

Referring now to the drawings wherein like reference numerals are used to identify like or identical components in the various views, FIG. 1 generally shows a catheter 10, provided in an undeflected state along longitudinal axis L. As illustrated, the catheter 10 includes a distal portion 12 and a proximal portion 14. As shown, the proximal portion 14 of catheter 10 may be rigidly connected or attached to a support base 16. In an embodiment, the support base 16 may be a portion of a disposable cartridge, and may be configured to interface with a robotic catheter manipulation assembly.

As generally illustrated, the catheter 10 may include two steering wires 18, 20, each longitudinally situated within and along a substantial length of the catheter body. In an embodiment, the steering wires 18, 20 may be comprised of a material having a high elastic modulus—such as, for example, steel or aluminum. The catheter 10 may further include a pull ring 22, which may take the form of a rigid ring firmly connected or affixed within a portion of the distal portion 12 of the catheter 10. Each steering wire may be rigidly connected to pull ring 22, for example, via a rigid connection or coupling 24, 26. In an embodiment, such a rigid connection or coupling may comprise a weld and/or other known means for suitable attachment.

As generally depicted in the illustrated embodiment, proximal portions of the steering wires 18, 20 may be respectively connected to control members 28, 30. Control members 28, 30 may be used, for example, to interface or operatively connect control devices with steering wires 18, 20. For illustrative purposes, as generally shown in FIG. 1, when catheter 10 is configured in an undeflected state on longitudinal axis L, control members 28, 30 may both be situated at a one or more initial or common reference levels or datum (e.g., common datum X shown in FIG. 1). However, for some embodiments, no initial relationship of control members 28, 30 is necessary, and the positioning of each may, for instance, simply be a consequence of initial assembly.

In an embodiment, catheter 10 further includes tip 32 that may be used to perform various medical treatments or procedures. In an embodiment, catheter tip 32 may include one or more mapping electrodes that can, for example, be used to detect physical or electrical characteristics of cardiac tissue. In an embodiment, tip 32 may include one or more ablation electrodes that can, for example, be used to create lesions within cardiac tissue during an ablation procedure. In an embodiment, tip 32 may include phased ultrasound arrays that may, for example, be used to sense various properties of cardiac tissue. Moreover, the invention is not limited to a particular catheter tip and embodiments of the invention may include various combinations of one or more of the aforementioned features.

Figure 2:
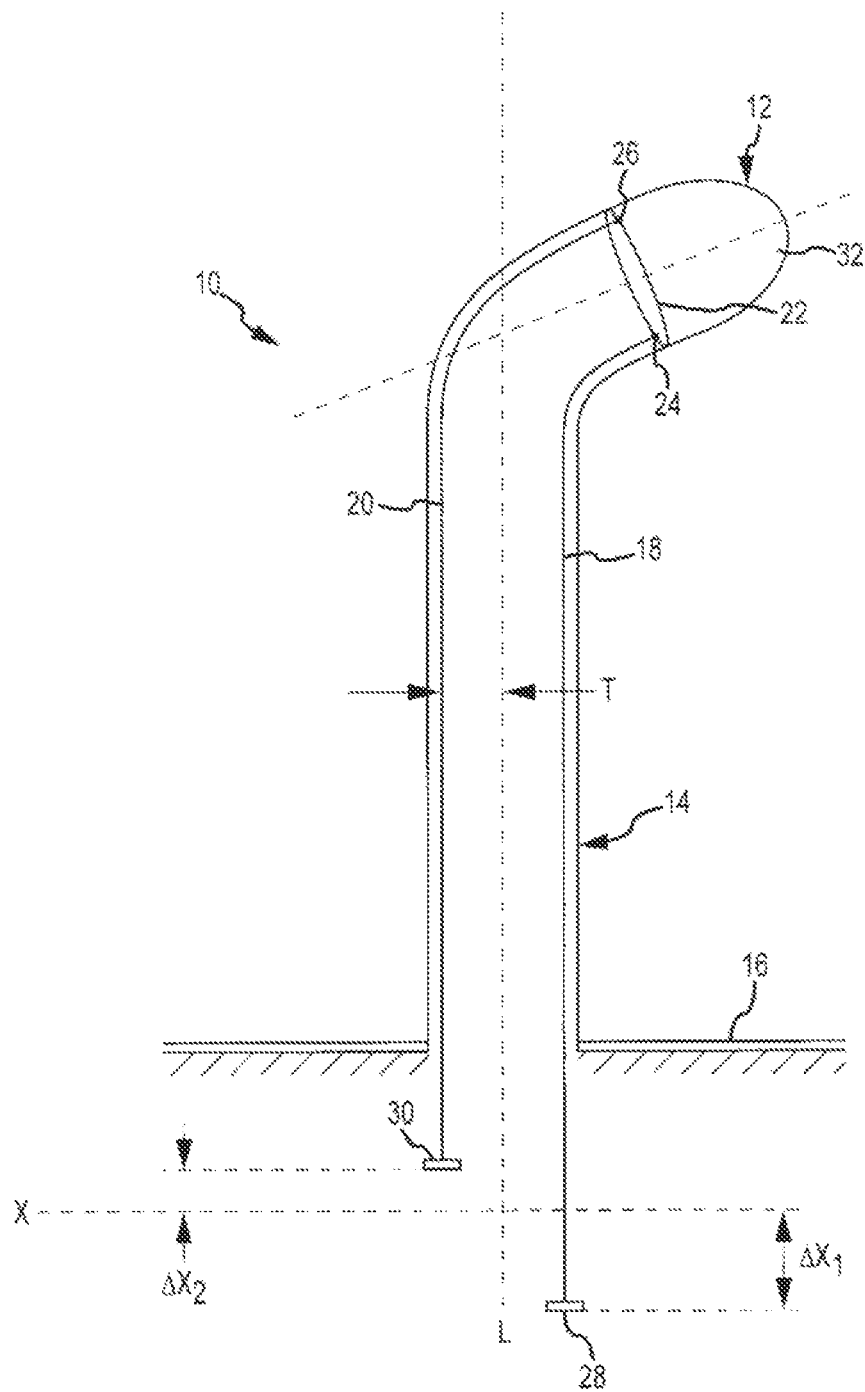
FIG. 2 is a general representation of a catheter of the type illustrated in FIG. 1, shown in a deflected state.

As generally shown in FIG. 2, the distal portion 12 of catheter 10 may be deflected or displaced away from longitudinal axis L by selective actuation or tensioning of one or more steering wires. For example, as generally illustrated in FIG. 2, control member 28 may be translated in a proximal direction a distance $\Delta X_1$, which causes a tension response in steering wire 18. The actuation of steering wire 18 causes a corresponding rotation and deflection of the distal portion 12 of catheter 10 in a direction toward steering wire 18.

As further illustrated in FIG. 2, while control member 28 is actively deflected a distance $\Delta X_1$ in a first proximal direction, control member 30 reactively moves or retracts a distance $\Delta X_2$ in a second, substantially opposing distal direction. The reactive motion of control member 30 and steering wire 20 may be a function of a transverse distance T between steering wire 20 and the central longitudinal axis L, along with a radius of curvature of distal portion 12. While, theoretically, displacements $\Delta X_1$ and $\Delta X_2$ can bear a linear relationship to each other, non-uniform axial compression of catheter 10 can cause the relationship between $\Delta X_1$ and $\Delta X_2$ to be non-linear.

To cause catheter 10 to move or retract back to an undeflected state along longitudinal axis L, a user could, for example, actively translate control member 30 in a proximal direction. Such a motion could cause the distal portion 12 to rotate and deflect toward steering wire 20, while control member 28 would be reactively translated in a distal direction. In an embodiment, due to some extent on memory effects of catheter 10, upon restoring catheter 10 to an undeflected state along longitudinal axis L, control members 28, 30 may not necessarily return to their original positions (e.g., on datum X).

Figure 3A:
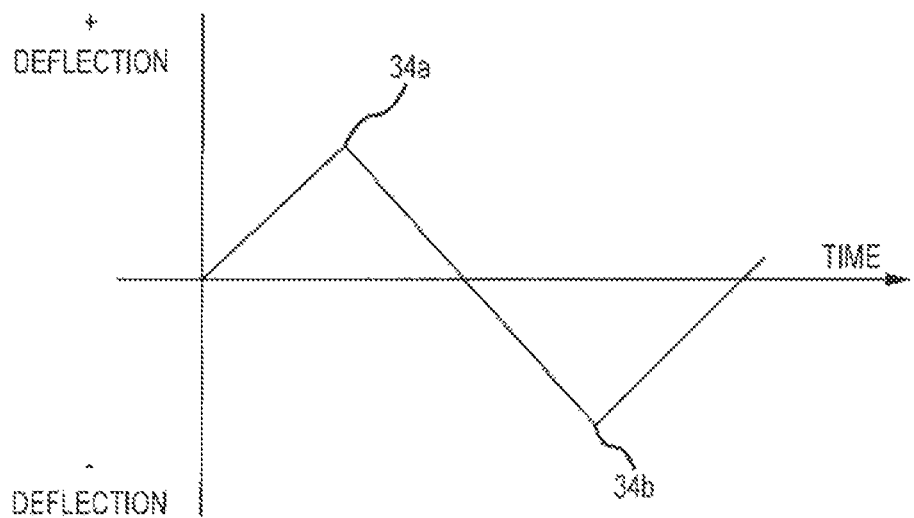
FIG. 3a is a graph that generally illustrates a dynamically responsive catheter motion.
Figure 3B:
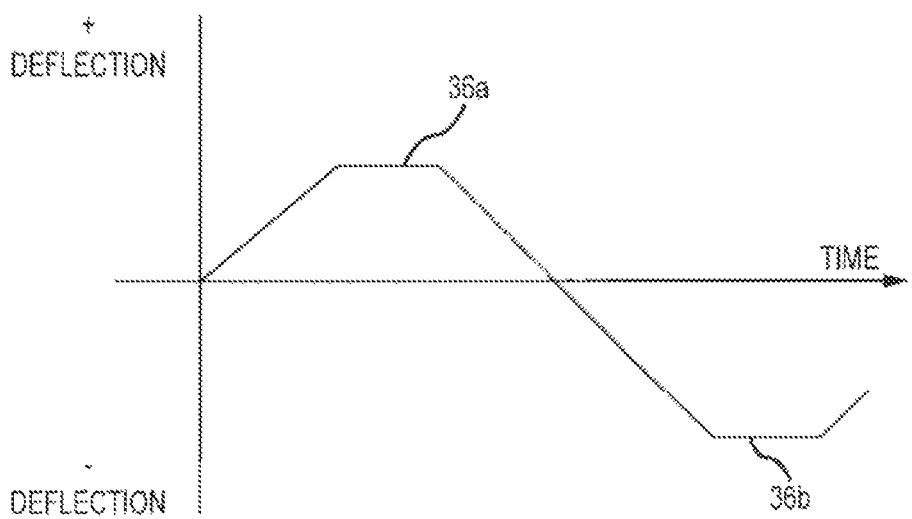
FIG. 3b is a graph that generally illustrates a catheter motion with transition latencies.

It may be desirable, for example during a medical procedure, for the distal portion of a catheter to be capable of prompt dynamic, back and forth movements. To help facilitate such movement, it can be beneficial to maintain a minimal tension on all steering wires, even when such a steering wire may be reactively translating in a distal direction. Such a base or minimal tension can help ensure that no undesirable measure of slack is created in any steering wire that could potentially cause an unresponsive state (even if only momentarily) during a transition from a motion in one direction to motion in another direction. FIG. 3a includes a graph that generally illustrates a desirable, dynamically responsive catheter motion. This graph demonstrates a motion with sharp transitions 34a, 34b between active and reactive steering wires. In contrast, FIG. 3b illustrates a catheter motion that exhibits somewhat undesirable unresponsive states 36a, 36b, which may be occasioned by a need to re-tension reactive steering wires during a transition period.

Figure 4:
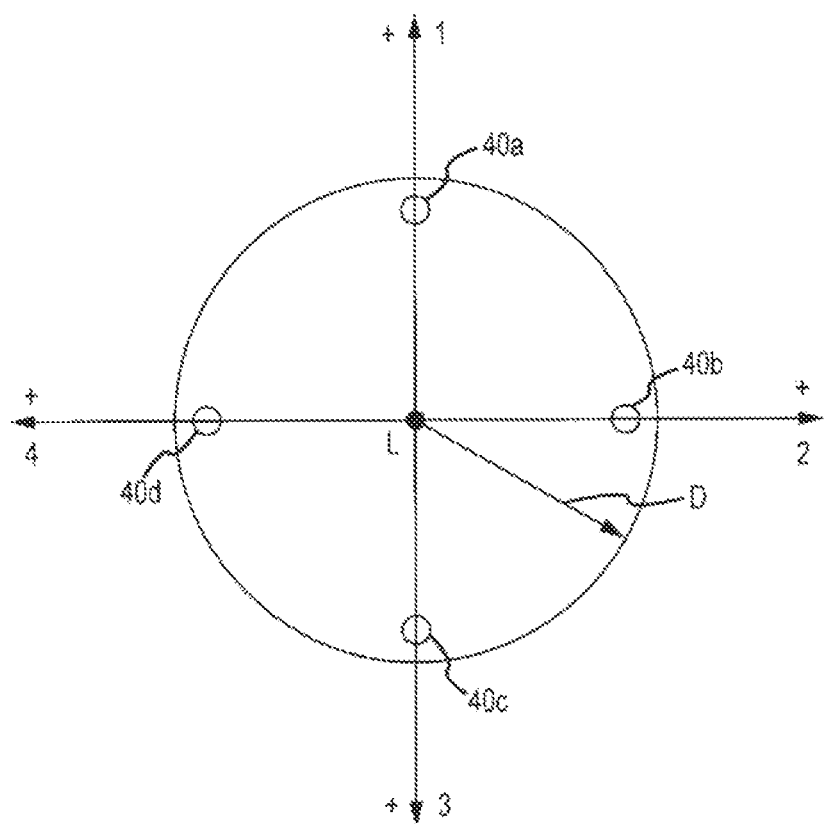
FIG. 4 is an axial cross-section of an embodiment of a catheter that includes four steering wires.

It is noted that while FIGS. 1-3 illustrated the operation of a catheter having two steering wires oriented in a planar configuration, other embodiments may include three or more steering wires to cause three dimensional motion of the distal portion of the catheter. FIG. 4 generally shows an axial cross-section of a catheter embodiment that includes four steering wires 40a, 40b, 40c, 40d. While this illustration displays all steering wires spaced approximately 90 degrees apart, various other configurations may be provided.

As generally illustrated in FIG. 4, the respective tensioning of adjacent steering wires may cause a deflection of the distal portion 12 of catheter 10 in a unique direction, e.g., direction D. Through selective actuation of pairs of steering wires, the distal portion of the catheter can be made to traverse circles of varying radii about longitudinal axis L (as viewed transverse to the page). The embodiment illustrated in FIG. 4 is similar to the two-steering wire embodiments shown in FIGS. 1-3, since, when any wire or wires are actively tensioned, the opposing wires is permitted to reactively move a distance in an opposing distal direction. For example, as shown in FIG. 4, to cause a distal motion in direction D, steering wires 2 and 3 (40b, 40c) may be positively tensioned, while steering wires 1 and 4 (40a, 40d) would move reactively.

Figure 5:
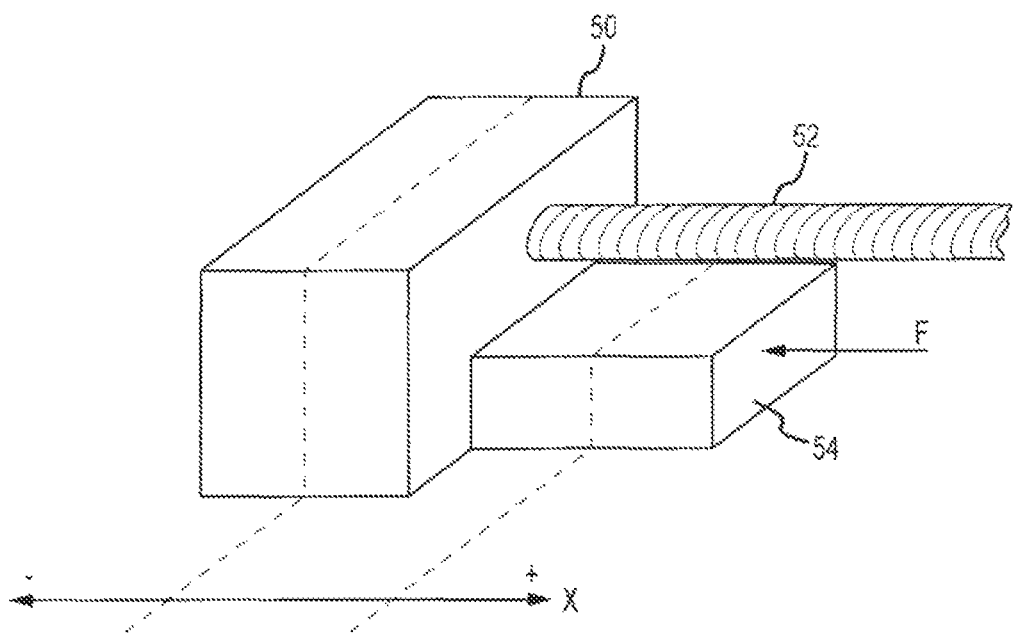
FIG. 5 is an isometric representation of a control element in adjoining contact with a control member.

FIG. 5 generally illustrates a potential relationship between control member 50, steering wire 52, and control element 54. In an embodiment, control member 50 and steering wire 52 may be rigidly attached, such that movement of control member 50 in the X− direction will cause a corresponding tensile force to be applied to steering wire 52. Similarly, a movement of control member 50 in the X+ direction may cause a corresponding compressive force to be applied to steering wire 52.

FIG. 5 generally illustrates a control element 54 in adjoining contact with control member 50, such that a movement of control element 54 in the X− direction will cause a corresponding movement of control member 50 in the same direction. In an embodiment, control element 54 may not be rigidly connected or attached to control member 50, and any translation of control element 54 in the X+ direction may result in a loss of contact between the control element 54 and control member 50.

Figure 6:
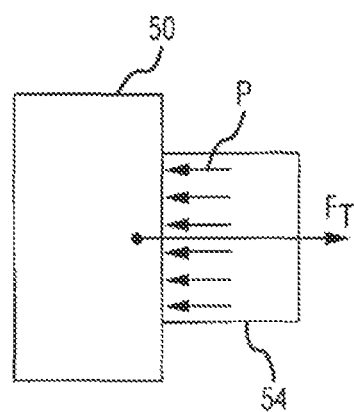
FIG. 6 is a free body diagram of an embodiment of a control member.

FIG. 6 includes a free body diagram of an embodiment associated with a control member 50. As generally illustrated, control member 50 may be acted upon my a contact force, in the form of a pressure P, from control element 54, and a tensile force $F_T$ applied from steering wire 52, though control member 50 may be free of all other external forces. Accordingly, in an embodiment, control member 50 may be a slider block that is free to passively translate in the X+ or X− directions solely as a result of the applied steering wire and control element forces.

In an embodiment, control member 50 may be similar to control members 28, 30, shown in FIGS. 1 and 2. In such an embodiment, control element 54 may be located distally to control member 50 (i.e. in an X+ direction as shown in FIG. 5), and may apply a contact pressure P on control member 50 to effectuate a proximal translation of control member 50 a distance ΔX. Moreover, in an embodiment, control element 50 may be actively translated via a coupled drive mechanism, for example as further described below.

In an embodiment where control member 50 is required to translate distally (as generally shown by control member 30 in FIG. 2), control element 54 may be configured to also translate distally to avoid impeding the associated reactive motion of control member 50. It is contemplated that control element 54 may simply break contact with control member 50, and return to a more distal "home" position that is assured not to impede the motion of control member 50. In such an embodiment, however, a latency may be created when contact must be re-established between control element 54 and control member 50 (e.g., as generally described above with reference to FIG. 3b). In another embodiment, control element 54 may be moved distally in a controlled manner to maintain a minimal contact force or pressure on control member 50 without significantly impeding its movement. In such an embodiment, the reactively moving control member could be maintained in a "ready" state such that it can transition to an active control member without associated latency.

Figure 7:
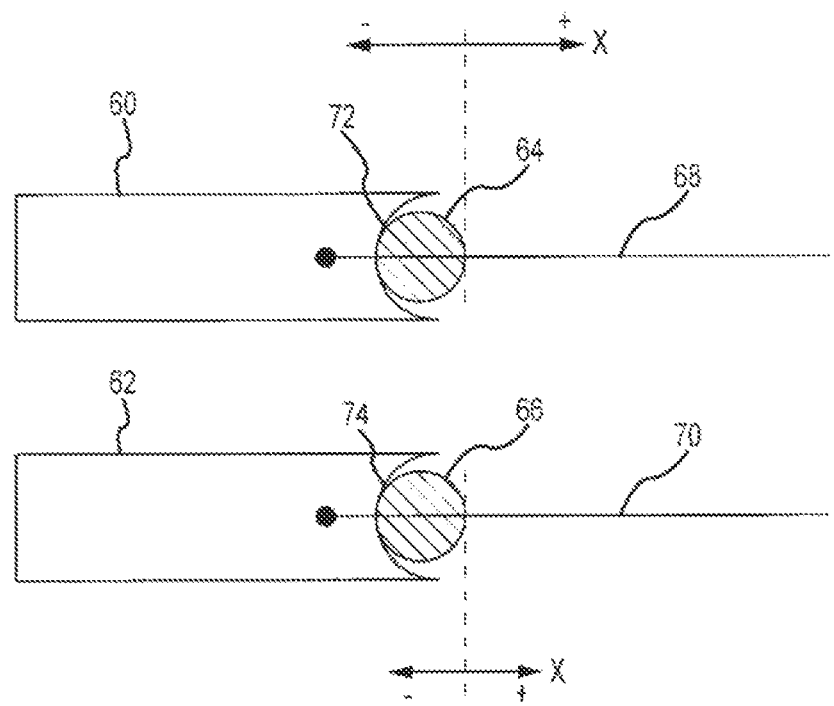
FIG. 7 is a general representation of a configuration of control members, control elements, and steering wires according to an embodiment of the invention.

FIG. 7 generally illustrates a configuration of another embodiment of control members 60, 62, control elements 64, 66, and steering wires 68, 70. In this embodiment, the contact portions or surfaces between control members 60, 62, and respective control elements 64, 66 may be geometrically configured such that the control elements may self-center along the contact surface of the control members (or vice versa). Such a configuration may assist the interface between the control elements and control members and help minimize off-center resultant forces and corresponding moments. In an embodiment, as generally illustrated in FIG. 7, one or both control members 60, 62 may include a geometrically concave contact interface surface 72, 74. Correspondingly, one or both control elements 64, 66 may include a geometrically convex contact interface surfaces configured to mate with a portion of a concave contact interface surface 72, 74. It is contemplated that other geometric configurations may also be used for the purpose of creating an efficient and repeatable force transfer between a control element 64, 66 and respective control member 60, 62.

Figure 8A:
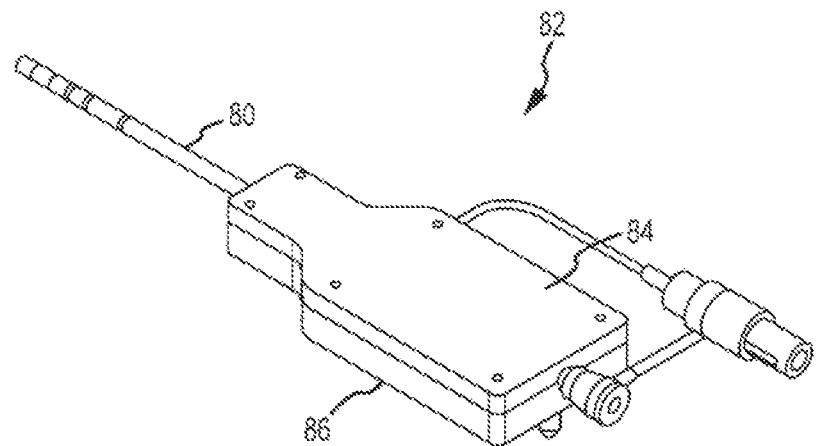
FIG. 8a is an isometric view of a device cartridge connected to a catheter body according to an embodiment.
Figure 8B:
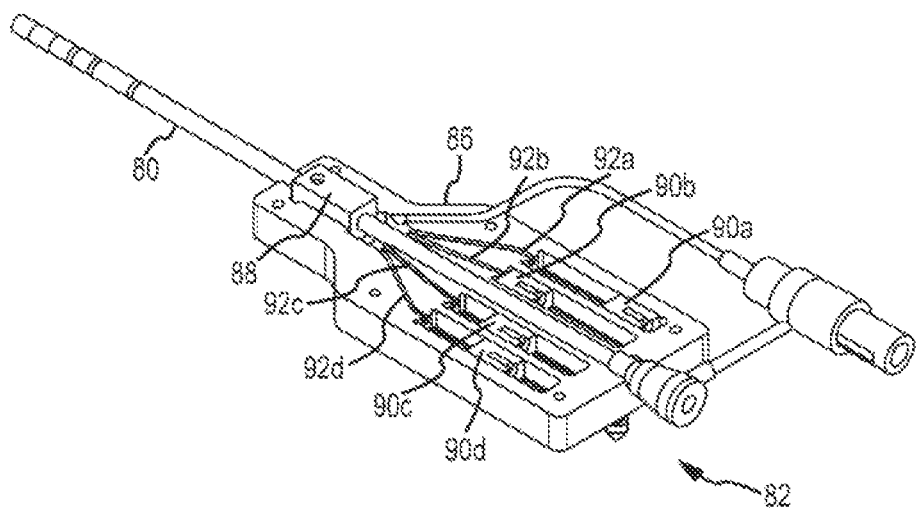
FIG. 8b is an isometric view of the device cartridge shown in FIG. 8a with an upper portion removed.
Figure 8C:
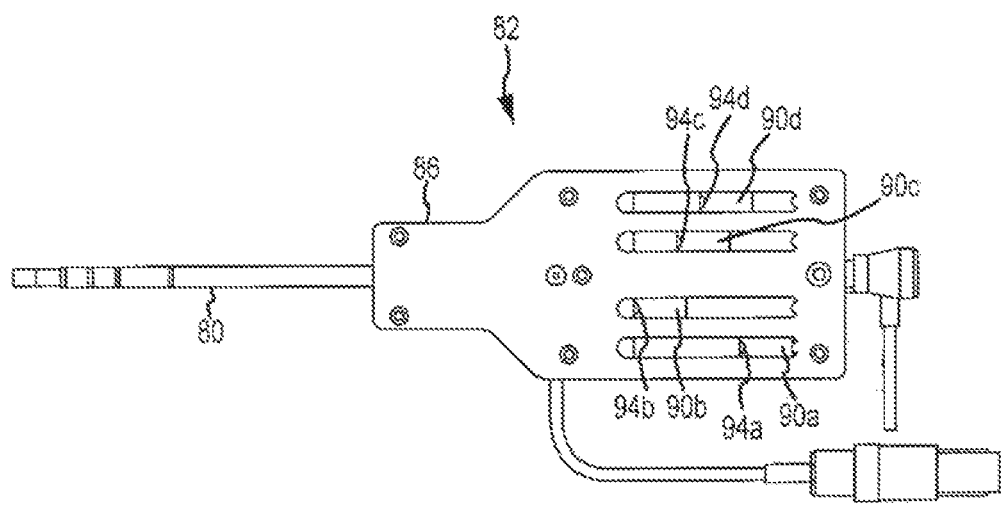
FIG. 8c is bottom view of the lower portion shown in FIGS. 8a and 8b.

In an embodiment, such as generally shown in FIGS. 8a, 8b, and 8c, catheter body 80 may interface with a device cartridge 82. As illustrated in FIG. 8a, in an embodiment, device cartridge 82 may comprise an upper portion 84, and a lower portion 86. As generally shown in FIG. 8b, in an embodiment, catheter body 80 may extend distally from a proximal support base 88 to which it may be rigidly connected or coupled. In an embodiment, the lower portion 86 of device cartridge 82 may, for example, be configured to house a plurality of slidable control members 90a, 90b, 90c, 90d, such as those described above in connection with FIGS. 5-7.

In an embodiment, lower portion 86 of device cartridge 82, and slidable control members 90a, 90b, 90c, 90d, are configured to minimize static friction, which may result in sliding non-linearities. In an embodiment, for example, lower portion may be made from a smooth polycarbonate material, while slidable control members 90a, 90b, 90c, 90d may be made from a friction-resistant material such as, for example, Delrin-AF. Moreover, while FIG. 8b illustrates an embodiment with four slidable control members 90a, 90b, 90c, 90d, the invention is not limited to the configuration shown or the number of control members, and other configurations and numbers are contemplated by the invention. Further, FIG. 8b illustrates steering wire guide channels 92a, 92b, 92c, 92d that may provide for the passage of the four respective steering wires from the proximal support base 88 to the respective slidable control members 90a, 90b, 90c, 90d.

FIG. 8c generally illustrates the underside of the lower portion 86 of device cartridge 82, shown in FIGS. 8a and 8b. As generally shown in FIG. 8c, slidable control members 90a, 90b, 90c, 90d may each include distally oriented, concave interface surfaces 94a, 94b, 94c, 94d—for example, such as those previously described in connection with FIG. 7.

Figure 9:
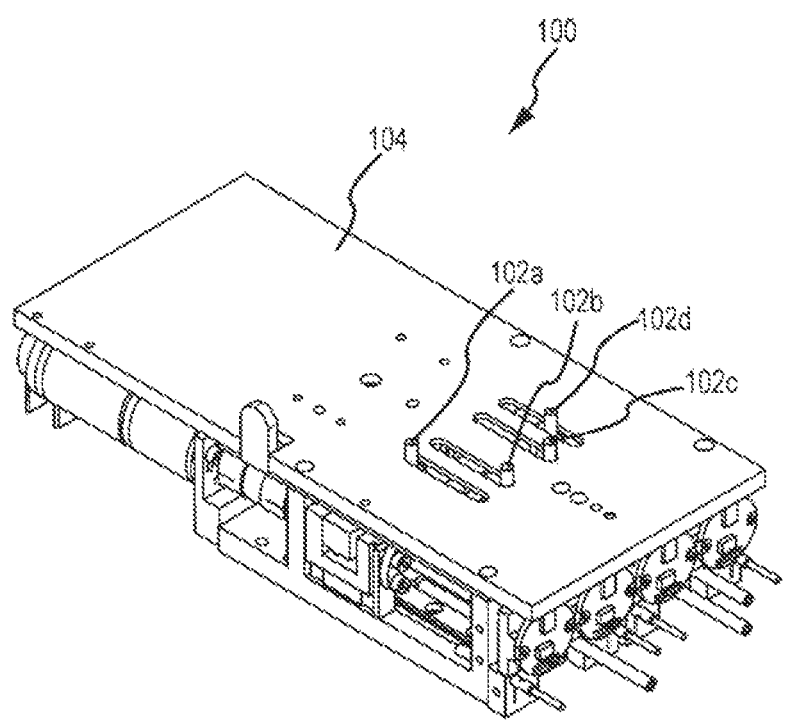
FIG. 9 is an isometric view of an embodiment of a manipulator assembly.

With reference to FIG. 9, it is noted that a device cartridge may be configured to couple with a manipulator assembly 100. As shown in the illustrated embodiment, manipulator assembly 100 may include a plurality of control elements 102a, 102b, 102c, 102d, that transversely extend beyond a control surface 104. In an embodiment, each control element 102a, 102b, 102c, 102d may have a geometrically convex shape that can be configured to interface with a respective concave interface surface 94a, 94b, 94c, 94d of slidable control member 90a, 90b, 90c, 90d.

FIGS. 5-9 generally illustrate embodiments and methods of interfacing a distally located control element with a more proximally located control member, such that the control element may push the slidable control member proximally to maintain a tension. However, it should be noted that other means of interfacing a control element with a control member are also contemplated. For example, without limitation, a control element may be configured to grip and translate an appropriately configured control member to cause a proximal motion of the control member. Further, in an embodiment, a control element may be configured to fit within a recess of an appropriately configured control member to effect bi-directional linear motion (proximal or distal) of the control member. In another embodiment, the control element may be distally located with respect to the control member and include a latching mechanism that may be capable of pulling the control member in a proximal direction. Furthermore, all linear, directional movement of control members is described with reference to a connected or attached steering wire rather than the associated catheter body. As such, in an embodiment, the slidable paths of the various control members (e.g., those illustrated in FIGS. 8a, 8b, and 8c) may be respectively angled such that the control members do not necessarily translate linearly with respect to the longitudinal axis of the catheter body.

Figure 10:
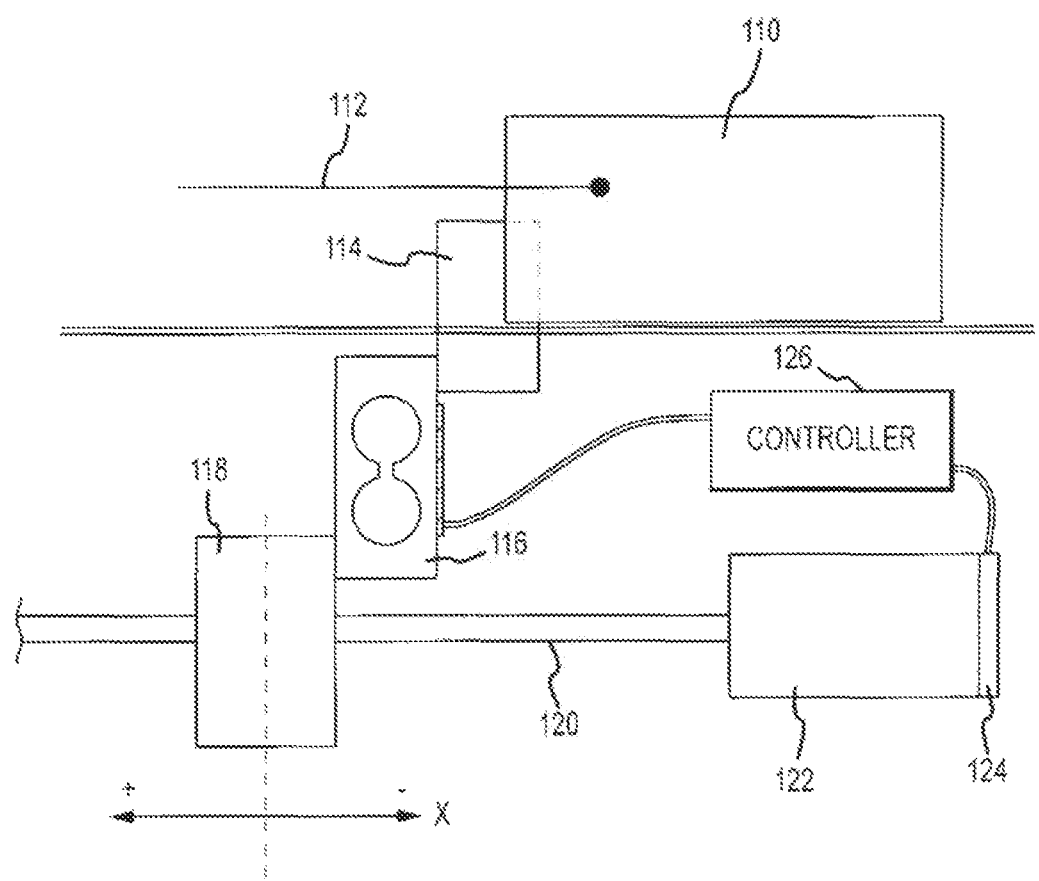
FIG. 10 is a representation of a system in accordance with an embodiment of the invention.

FIG. 10 generally illustrates a representation of an embodiment of a system in accordance with teachings of the invention. The illustrated system includes a slidable control member 110 that is connected to or coupled with a steering wire 112. The control member 110 may be configured to interface with a corresponding control element 114. In an embodiment, control element 114 may further be operatively coupled with a portion of a sensor 116, which, in turn, may be coupled with a translatable drive element 118 that can be mechanically moved. For example, without limitation, translatable drive element 118 may ride on or may otherwise be mechanically moved by a mechanical movement device 120, such as a drive screw, that, in turn, may be coupled with a motor 122. In an embodiment, motor 122 may further be in communication with an encoder 124. In an embodiment, mechanical movement device 120 may include a lead screw, and translatable drive element 118 may include a threaded nut. In another embodiment, mechanical movement device 120 may include a ball screw, while translatable drive element 118 may include a ball assembly. In further embodiments, mechanical movement device 120 may include a motor driven belt drive, a voice coil, a rolling ring linear drive, or a piezo motor drive. In an embodiment, sensor 116 may include a piezoelectric force sensor, a thin film force sensor, a magnetic force restoration sensor, a or strain gauge such as, for example, a 12 pound S215 load cell commercialized by Strain Measurement Devices, Inc.

In an embodiment, translatable drive element 118 may be controllably translated by a mechanical movement device 120 (e.g., a drive screw) in the X+ or X− directions. Further, a position sensor may be coupled to the translatable drive element 118 to provide the system with an indication of the location of drive element 118 along the X axis. The position sensor may operate in either absolute or relative coordinates. In an embodiment the position sensor may comprise an encoder 124. In another embodiment, the position sensor may comprise a linear encoder (not shown) coupled directly with the translatable drive element 118. In a further embodiment, the position sensor may include a potentiometer configured to provide a varying voltage output, proportional to the position of the translatable drive element 118.

In the embodiment generally illustrated in FIG. 10, sensor 116 may be configured to provide an indication of a force exerted on or in connection with control element 114. Such an indication of a force may, for example, be provided if, during operation, control member 110 is urged in a distal direction by steering wire 112, and control element 114 was in interfaced with control member 110 in a contacting relationship. This indication of the contact force between the control element 114 and control member 110 may be provided to a controller 126, for example, to be measured or evaluated. In such an instance, the measured force may be reduced or eliminated if translatable drive element 118 were to be translated by motor 122 and associated drive screw 120 in an X+ direction (i.e., in the direction of the distally applied steering wire tension). Likewise, such a measured force may be increased if translatable drive element 118 were to be translated in an X− direction (i.e., in the direction counter to the distally applied steering wire tension).

In an embodiment, controller 126 may be configured to control the operation of motor 122 in response to a measured contact force between control element 114 and control member 110. In such a configuration, the controller 126 may help serve to ensure that a minimal tension is maintained on all steering wires, even when such a steering wire may be reactively translating in a distal direction (e.g., as previously described in connection with FIGS. 2-4). Such a tension may help prevent undesirable slack from forming in connection with steering wires, which could for instance cause an unresponsive state or condition during a transition from motion in one direction to motion in an opposite direction. In an embodiment, controller 126 may be configured to control the operation of the mechanical movement device 120 in a continuous or substantially continuous manner to avoid the application of step-wise or non-linear tension on steering wire 112. While FIG. 10 generally depicts the contact force sensor 116 as a strain gauge, other means of contact force sensing, as known in the art, may be used and are likewise contemplated. Such means may include, for example, without limitation, the use of a piezoelectric force sensor, a thin film force sensor, or a magnetic force restoration sensor.

Figure 11A:
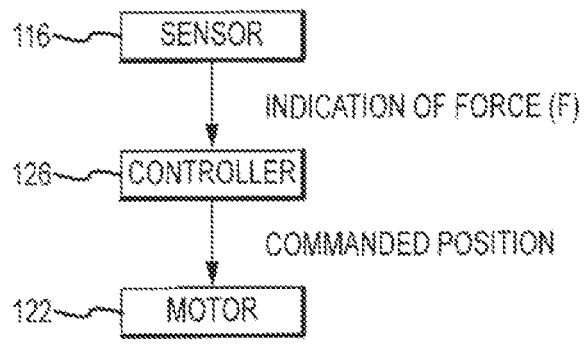
FIGS. 11a and 11b are flowcharts generally illustrating different methods in which a controller may control the linear position of a translatable drive element in response to a contact force between a control element and a control member.
Figure 11B:
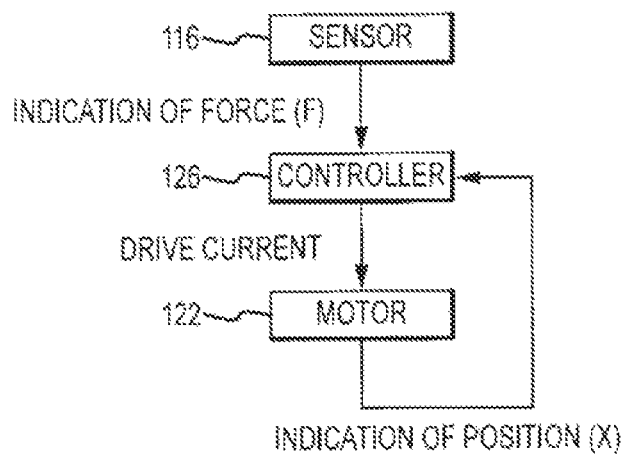

FIGS. 11a, 11b generally illustrate two methods in which a controller 126 may control the linear position of a translatable drive element 118 in response to a contact force between a control element 114 and a control member 110. FIG. 11a depicts a general control algorithm where the controller 126 first receives an indication of contact force (F) from a sensor 116. The controller 126 may then command motor 122 to translate drive element 118 to a specific position based on the sensed force. Such a scheme may be useful, for example, where the motor 122 includes a stepper motor capable of moving to a known position.

FIG. 11b depicts a general control algorithm where the controller 126 receives an indication of contact force (F) from the sensor 116. The controller 126 may then provide motor 122 with an appropriate drive current to cause a movement (e.g., rotation) of a mechanical movement device 120 (e.g., a drive screw) and an associated movement or translation of drive element 118. The controller 126 may then receives an indication of the position of the drive element 118 from an encoder 124 associated with the motor 122 and/or a position sensor (e.g., as generally described above) and calculate an associated drive current in a closed-loop manner.

Figure 12:
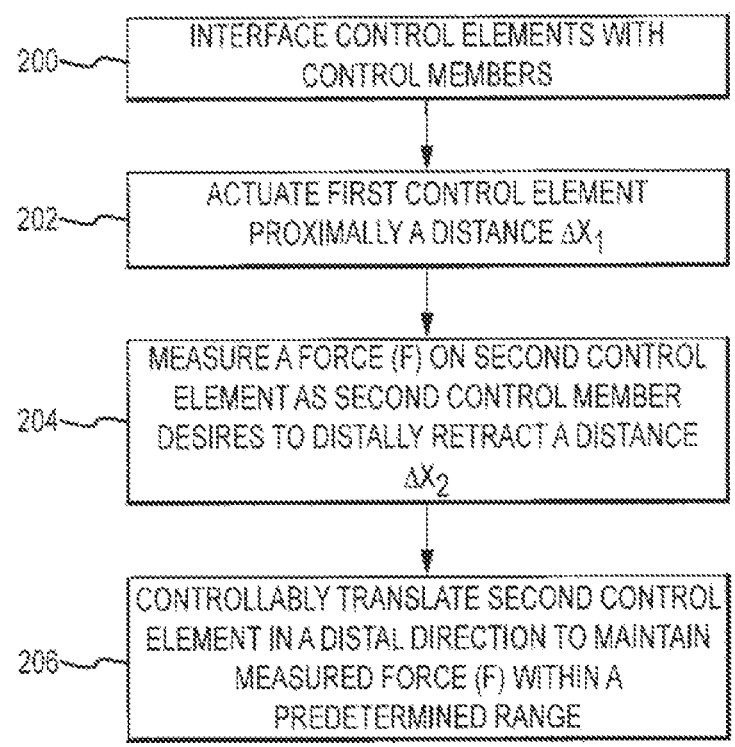
FIG. 12 is a flowchart of a tensioning scheme in accordance with an embodiment of the invention.

FIG. 12 provides a flow chart of the tensioning scheme of the type generally described above in relation to FIG. 10. In step 200, the control elements are first interfaced with respective control members. In an embodiment, the control elements commence or begin service or operation in an extreme distal configuration and not in contact with the respective control members. The manipulator assembly must then translate the respective control elements proximally until an initial contact with the control members has been made.

In step 202, a first control element is translated proximally a distance $\Delta X_1$ to cause a respective control member/steering wire movement, and to further cause a deflection of the distal portion of the catheter (e.g., as generally illustrated in FIG. 2). In step 204, the controller measures a force (F) applied against a second control element by a respective second control member. In an embodiment, the second control member is urged to distally retract a distance $\Delta X_2$ (e.g., as generally illustrated in FIG. 2), but is however prevented from retracting by the physical presence of a second control element.

In step 206, the controller controllably translates the second control element in a distal direction while maintaining a measured contact force within a pre-determined or acceptable range. As described above, if the measured force is higher than the pre-determined or acceptable range, a second control element may translate in a distal direction to alleviate some contact pressure. Likewise, if the measured force is below the pre-determined or acceptable range, the second control element may translate in a proximal direction to either re-establish contact with the control member, or to re-tension the steering wire to a minimal or desired level of tension. By way of example, without limitation, the pre-determined or acceptable range may comprises a minimal force designed to not significantly impede the distal motion of the catheter, or cause any undue axial loading on the catheter body, such as 50-100 grams of force.

Figure 13:
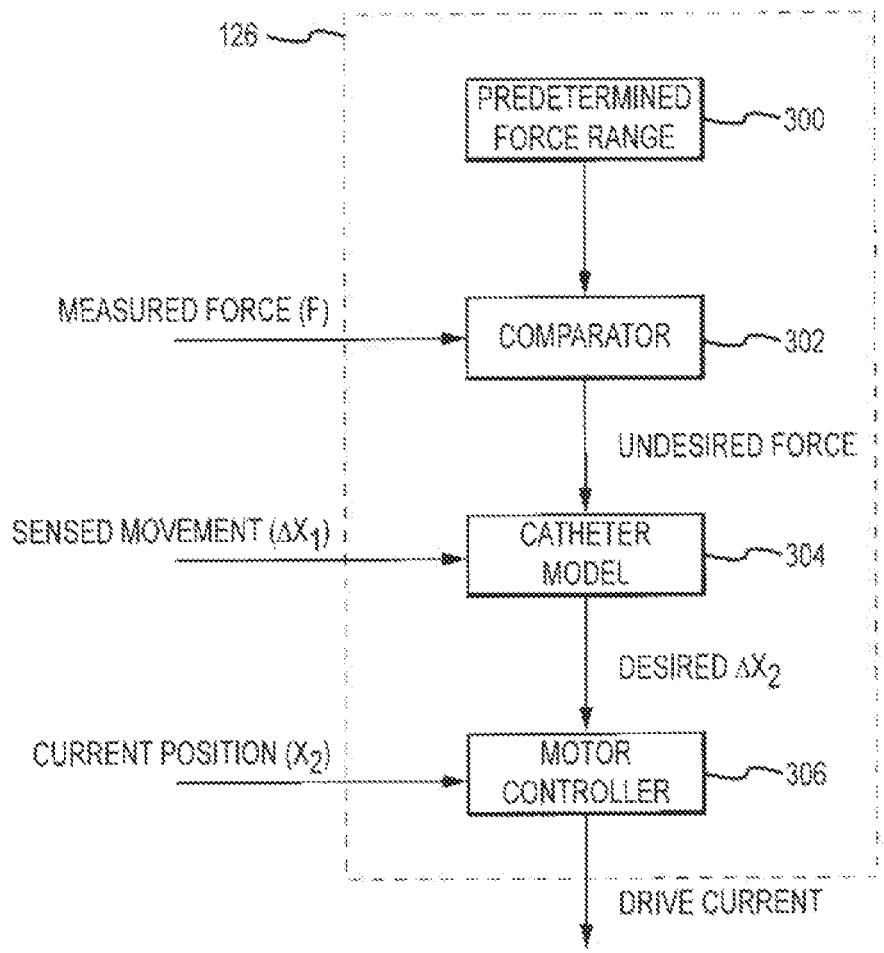
FIG. 13 is a flowchart of features associated with an embodiment of a controller.
Figure 14:
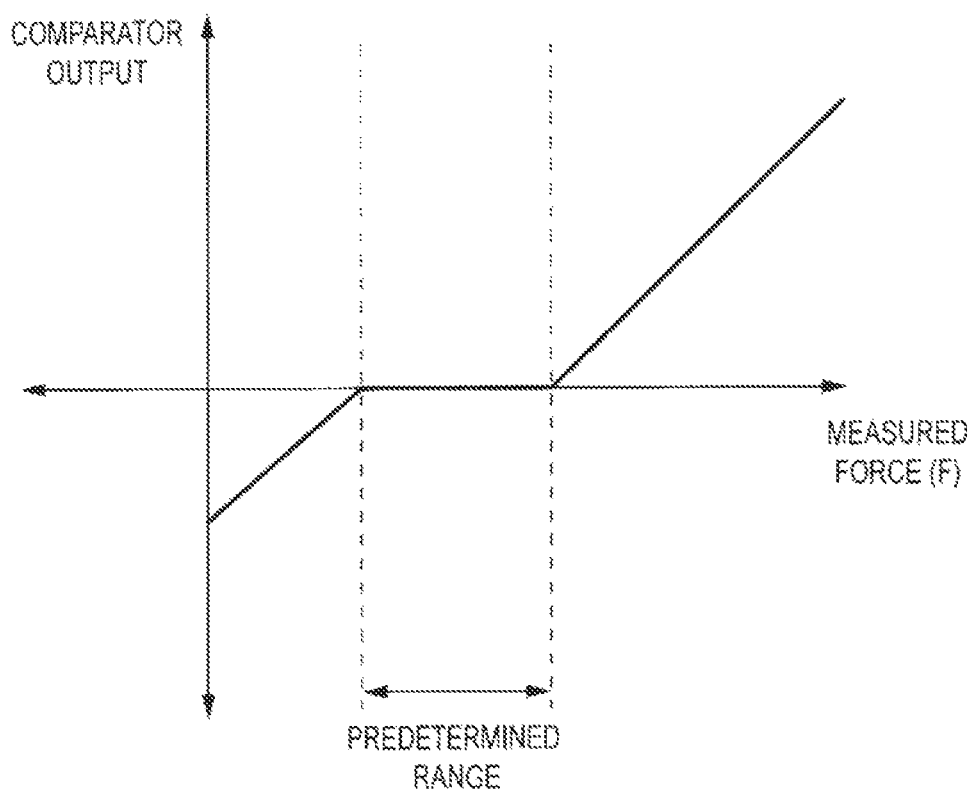
FIG. 14 is a graph of comparator output by measured force according to an embodiment.

FIG. 13 generally illustrates an embodiment of controller 126. In the illustrated embodiment, comparator 302 compares a measured force, provided by sensor 116, to a predetermined force range 300. In an embodiment, comparator 302 may provide an output that represents an undesired force (or lack thereof) applied on the control element. In such an embodiment, for example as shown in FIG. 14, the comparator output may equal the measured force (F) minus an upper bound of the range, if the force exceeds the range. If the measured force (F) is lower than the range, the comparator output may equal the measured force minus the lower bound of the range. Further, if the measured force (F) is within a predetermined range, the comparator output may equal zero.

As further illustrated by FIG. 13, in an embodiment, controller 126 may further include a catheter model 304 that serves to approximate a desired distal retraction $\Delta X_2$ as a function of either an undesired force, a sensed movement of the first control member a distance $\Delta X_1$ (as generally shown in FIG. 2), or both. The desired distal retraction of the reactive steering wire $\Delta X_2$ may then be provided to a motor controller 306 to ultimately provide a drive current to motor 122. In an embodiment, motor controller 306 may also receive an indication of the current position $X_2$ of the control element/control member via a position sensor (e.g., as described above). Motor controller 306 may use control techniques well known in the art to control the drive current provided to motor 122. Such techniques may include, for example, proportional, derivative, and/or integral control.

In an embodiment (not shown), controller 126 may be further configured to compute the derivative of sensed force with respect to time ($\delta F/\delta t$) and/or position ($\delta F/\delta X_2$). In an embodiment, the position derivative of sensed force ($\delta F/\delta X_2$) may be used, for example, to accurately determine when initial contact has been established between a control element and the respective control member, and "zero" the sensed force at that point.

Figure 15A:
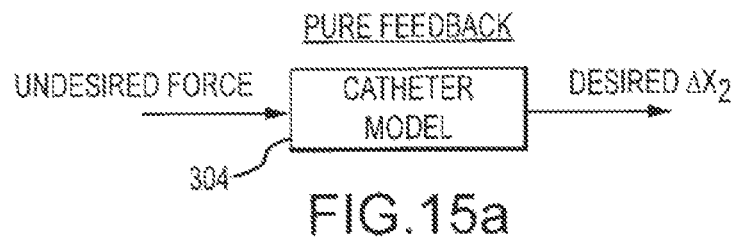
FIGS. 15a, 15b, and 15c generally illustrate, in a block form, various inputs and outputs associated with catheter models in accordance with embodiments of the invention.
Figure 15B:
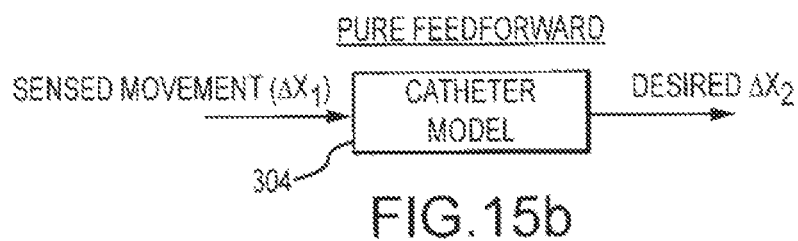
Figure 15C:
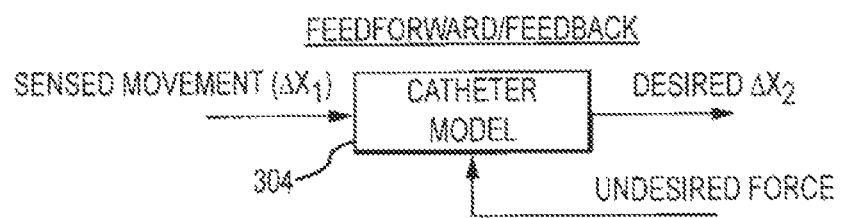

As illustrated in FIGS. 15a, 15b, 15c, catheter model 304 may incorporate various inputs in an effort to obtain or compute a desired $\Delta X_2$ with the greatest accuracy and least response lag. As generally shown in FIG. 15a, catheter model 304 may be purely reactionary and rely solely on feedback from a force sensor. As generally shown in FIG. 15b, catheter model 304 may instead be proactive and rely on the movement of $\Delta X_1$ and the physical properties/kinematics of the catheter design (i.e., feedforward). For some embodiments, a pure feedforward control model may provide less lag than a pure feedback control model. Finally, as generally shown in FIG. 15c, catheter model 304 may incorporate aspects of both feedback and feedforward models. For simplicity in the computational design, when incorporating a feedforward/feedback catheter model, a linear kinematic catheter model may be used with the assumption that the feedback will reduce or eliminate any associated model errors. Specifics of the catheter model will vary with the type and complexity of the catheter selected.

Although embodiments of this invention have been described above with a certain degree of particularity, those skilled in the art could make numerous alterations to the disclosed embodiments without departing from the spirit or scope of this invention. For example, while embodiments have been described using strain gauges, it is to be understood that additional embodiment could include other types of sensors and encoders including, without limitation, absolute position encoders, relative position encoders, optical encoders, linear encoders, linear actuators, and linear variable differential transformers. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed:

1. An apparatus for maintaining a robotic catheter system in a responsive state comprising:
   a catheter including a proximal portion, a distal portion, and at least two steering wires, the steering wires configured at one end to control the movement of at least a portion of the distal portion of the catheter and at the other end for connection to a control member;
   a plurality of control elements, each control element configured to engage or interface with a respective control member; and
   a controller configured to measure a force exerted on at least one control member by the respective control element, and further configured to translate the control element based on the measured force to substantially maintain the force exerted on the at least one control member within a select or determined range;
   wherein the control element remains proximate to the respective control member such that the system is maintained in a responsive state.

2. The apparatus of claim 1, further comprising a force sensor coupled with the control element and configured to provide an indication of the force exerted on at least one control member by the respectively interfaced control element.

3. The apparatus of claim 2, wherein the force sensor comprises a strain gauge, a piezoelectric force sensor, a thin film force sensor, or a magnetic force restoration sensor.

4. The apparatus of claim 1, further comprising a position sensor configured to provide a position of a respective translatable control element.

5. The apparatus of claim 4, wherein the controller is further configured to receive an indication of the position of the control element from the position sensor and to effectuate or command a translation of the control element to a desired position.

6. The apparatus of claim 5, wherein the desired position is provided or derived, at least in part, from the indication of the position of the control element provided by the position sensor.

7. The apparatus of claim 1, further comprising a mechanical movement device configured to controllably translate at least one respective control element wherein the mechanical movement device operates in response to commands received from the controller.

8. The apparatus of claim 1, further comprising a mechanical movement device configured to controllably translate at least one respective control element wherein the mechanical movement device comprises a motor driven lead screw, a motor driven ball screw, a motor driven belt drive, a voice coil, a rolling ring linear drive, or a piezo motor drive.

9. The apparatus of claim 1, further comprising a mechanical movement device configured to controllably translate at least one respective control element wherein the controller is further configured to operate the mechanical movement device in a continuous or substantially continuous manner.

10. The apparatus of claim 1, wherein the force exerted on at least one control member by the respectively interfaced control element is a contact force exerted in a direction distally oriented with respect to the control member.

11. The apparatus of claim 1, wherein each control element is unconnected to the steering wires and to each respective control member.

12. The apparatus of claim 1, wherein each control element is configured to apply a contact force on each respective control member in a first direction; wherein each steering wire is configured to apply a tensile force on each respective control member in a second direction; and wherein the first direction is different than the second direction.

13. A method of maintaining a robotic catheter system in a responsive state comprising:
  providing a catheter with a plurality of steering wires extending longitudinally therein, each steering wire including a proximally located control member;
  providing a plurality of control elements;
  interfacing at least two control elements with at least two respective control members;
  measuring a force exerted on at least one control member by the respectively interfaced control element; and
  controlling the motion of the at least one control element based on the measured force to maintain the measured force within a select or determined range, wherein the control element remains proximate to the respective control member such that the system is maintained in a responsive state.

14. The method of claim 13, wherein controlling the motion of the at least one control element comprises computing a desired position of the control element as a function of the measured force exerted on the respectively interfaced control member.

15. The method of claim 14, wherein controlling the motion of the at least one control element further comprises computing a desired position of the control element as a function of the measured force exerted by a second control element on a second control member.

16. The method of claim 14, wherein controlling the motion of the at least one control element further comprises commanding the at least one control element to translate to the desired position.

17. The method of claim 13, wherein interfacing at least one control element with at least one respective control member comprises distally positioning the control element with respect to the control member.

18. The method of claim 13, wherein interfacing at least one control element with at least one respective control member comprises establishing contact between each control element and control member.

19. The method of claim 13, wherein providing a plurality of control elements further comprises geometrically configuring at least one control element to interface with at least one respective control member.

20. The method of claim 19, wherein geometrically configuring at least one control element to interface with at least one respective control member comprises configuring the control element with a physically convex interface surface.

\* \* \* \* \*